US010309935B1

(12) United States Patent
Mohammed et al.

(10) Patent No.: US 10,309,935 B1
(45) Date of Patent: Jun. 4, 2019

(54) EVALUATING CONDITIONS ASSOCIATED WITH A MATERIAL HANDLING EQUIPMENT

(71) Applicant: Amazon Technologies, Inc., Seattle, WA (US)

(72) Inventors: Raashid Mohammed, Mercer Island, WA (US); Kevin Keck, Setttle, WA (US); David Bruce McCalib, Jr., Seattle, WA (US)

(73) Assignee: Amazon Technologies, Inc., Seattle, WA (US)

(*) Notice: Subject to any disclaimer, the term of this patent is extended or adjusted under 35 U.S.C. 154(b) by 324 days.

(21) Appl. No.: 15/266,769

(22) Filed: Sep. 15, 2016

(51) Int. Cl.
| | | |
|---|---|---|
| *G01N 29/22* | (2006.01) | |
| *G01N 29/36* | (2006.01) | |
| *H04N 5/232* | (2006.01) | |
| *G02B 27/01* | (2006.01) | |

(52) U.S. Cl.
CPC ........... *G01N 29/226* (2013.01); *G01N 29/36* (2013.01); *G02B 27/0172* (2013.01); *H04N 5/23238* (2013.01); *G02B 2027/0138* (2013.01)

(58) Field of Classification Search
CPC .... G01N 29/226; G01N 29/36; G01N 29/225; G02B 27/0172; G02B 2027/013
USPC ..................................... 73/658, 432.1, 865.9
See application file for complete search history.

(56) References Cited

U.S. PATENT DOCUMENTS

| | | | |
|---|---|---|---|
| 2009/0012667 A1* | 1/2009 | Matsumoto | .......... G05D 1/0251 701/26 |
| 2011/0228116 A1* | 9/2011 | Margalith | ............. G01J 3/2803 348/222.1 |

FOREIGN PATENT DOCUMENTS

DE       102009043525 A1 *  10/2010   ............... B07C 5/00

* cited by examiner

*Primary Examiner* — Justin Seo
*Assistant Examiner* — Rose M Miller
(74) *Attorney, Agent, or Firm* — Kilpatrick Townsend & Stockton LLP (57) ABSTRACT

Systems and methods for improving, among other things, the commission and maintenance checks of material handling equipment are described. In an example, sensor data may be generated based on movement of test equipment by a material handling equipment along a path between locations of a facility. The path may be associated with movement of an item by the material handling equipment. The sensor data may be associated with different conditions along the path. The test may include a plurality of sensors configured to generate the sensor data. Based on the sensor data, an indication of a location along the path and a condition may be provided. The condition may be associated with the location along the path and may affect movement of the item at the location. The indication may be provided to a user equipment that is remote from the test equipment.

20 Claims, 8 Drawing Sheets

EVALUATING CONDITIONS ASSOCIATED WITH A MATERIAL HANDLING EQUIPMENT

BACKGROUND

Various types of material handling equipment exist for handling items across a wide range of facilities. Generally, such equipment includes mechanical and/or electrical components for the movement, storage, control, and/or protection of items throughout manufacturing, distribution, consumption, and/or disposal. In an example, conveyor systems are deployed within a storage facility to move items within the storage facility.

Upon installation in a facility, the material handling equipment is typically commissioned. The commissioning may involve checking the actual installation against an installation design. Further, in operation, the material handling equipment is routinely checked for maintenance.

Generally, commission and/or maintenance checks involve visual inspection and review of documents to ensure the quality of the installation and operation. However, such checks may be subjective and may fail to identify certain unacceptable conditions. Additionally, the more complex the installation is, the more difficult the checks become, thereby further exacerbating the quality of the checks. In certain situations, the checks may be even hard to complete unless complex equipment is used. In turn, lower quality checks may result in a lower quality of installation and/or operation, thereby increasing the risk of improper item handling and lowering the throughput of the material handling equipment.

To illustrate, consider an example of a long conveyor belt (e.g., length of multiple miles) running at different heights through a large warehouse. A visual inspection may be time consuming and subjective. The inspection quality further deteriorates for portions of the conveyor belt running at a high height (e.g., higher than the eye level of an inspector). Accordingly, many unacceptable installation or operation conditions may be missed, resulting in improper handling operations and failures.

BRIEF DESCRIPTION OF THE DRAWINGS

Various embodiments in accordance with the present disclosure will be described with reference to the drawings, in which.

DETAILED DESCRIPTION

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Systems and methods for improving, among other things, the commission and maintenance checks of material handling equipment are described herein. In an example, test equipment may be deployed to perform a check. The check may replace or supplement visual inspections and/or other types of existing checks. The test equipment may speed up the check and/or improve the quality, thereby reducing the overall risk of improper installation and operation and the risk of damage to items while also increasing the throughput of the material handling equipment. On one hand, the increased speed may stem from an automation of the check, from a design of the test equipment to mirror dimensions of an item, and from a visualization of the results of the check at a user interface. Because of the dimensions, the material handling equipment may handle the test equipment in the same or similar manner for handling other items. During the handling, the test equipment may test for different conditions. Indications about the conditions may be presented at the user interface. On the other hand, the improved quality may stem from a design of the test equipment to include multiple types of sensors for sensing various conditions and correlating these conditions with specific locations. A wide range of sensor types may be integrated in the test equipment, thereby enabling to detect conditions that would otherwise not be detectable via the visual inspection and/or other existing techniques. Because condition-location correlations may be tracked, if a condition is unacceptable, the corresponding location may be immediately identified and troubleshot.

In an example, the material handling equipment may be installed to move items along a path between locations within a facility. Various electrical and mechanical components (e.g., motors, robotic arms, conveyor belts, rollers, and the like) may handle the movement. The test equipment may be placed along the path and may be handled in a similar manner. While in motion along the path, the test equipment may generate different sensed data indicative of conditions along the path. These conditions may be associated with the electrical and mechanical components. In parallel, the test equipment may also generate location data and/or image data. The image data may be generated from an image sensor and may capture images about the sensed data and/or the locations. The sensed data may be synchronized with the location data and/or the image data. The test equipment may generate test data based on the synchronization. Additionally, or alternatively, the test data may be generated by a computing service remote from the test equipment upon receipt of the various types of data. The test data may include any or a combination of the sensed data, location data, and the image data. Generally, the test data may indicate the conditions and the locations and may enable a visualization (or some other presentation) of the sensed data, the conditions, and/or the locations. In an example, the test data may be visualized at a user interface hosted on user equipment. The visualizations may enable a review of the conditions and an identification of any unacceptable conditions and their respective locations. In another example, the test data may be further processed based on historical test data, historical conditions, and historical root causes to automatically identify unacceptable conditions and the root causes of such conditions. The unacceptable conditions and/or the root causes may be additionally, or alternatively, presented at the user interface.

In an illustration, consider an example of a conveyor system installed in a storage facility. The test equipment may include a temperature sensor, an impact sensor, a camera device, and displays, among many other sensors and components. One of the displays may show temperature readings of the impact sensor. Another display may show impact readings of the impact sensor. The two displays may be positioned around the camera device (e.g., within the camera device's field of view). The camera device may be a three-hundred sixty degree virtual reality camera. The test equipment may be placed along the conveyor belt. While travelling, the sensors may sense temperature and impact data. This sensed data may be shown as temperature and impact readings on the displays. Camera device may capture a video of the readings along with the surrounding environment. The test equipment may stream the video to a server. An inspector may wear and operate a virtual reality (VR) headset coupled to the server. Rather than having to walk and visually inspect the conveyor system, the inspector may play the video on the VR headset. The video may show a sudden change to a temperature reading a location where an electrical motor is installed. The sudden change may correspond to an unacceptable condition of the electrical motor overheating. Accordingly, the video may indicate the unacceptable condition (e.g., the sudden change in the reading) and the location (e.g., based on the surrounding environment shown in the video at the time of the sudden change). Similarly, the video may capture a sudden change in an impact reading at a location, where two sides of the conveyor system meet at a particular angle. As captured in the video, this sudden change that the particular angle at the adjoining location may be acute and unacceptable.

In a further illustration, consider the example where the analysis of temperature-related conditions may be automated. The automation may be similarly applied to impact data, other sensed data, and/or a combination of the different types of sensed data. The test equipment may include a location sensor or some other means to identify its location on the conveyor system. While travelling, the test equipment may generate the temperature data and location data, where the two data types may be synchronized. A baseline data may be accessed. The baseline data may represent a baseline signature identifying an acceptable range of changes to the temperature. At any particular location, the sensed temperature at that location may be compared to the respective baseline data. The comparison may be performed locally at the test equipment or remotely at the server. If the deviation is too large (e.g., more than two degrees Fahrenheit), an unacceptable temperature condition may be detected. An indication that identifies the location and this unacceptable condition may be generated. In addition, a video frame or a video segment showing the location may be associated with the indication. The indication and the associated video frame(s) may be sent to the VR headset for presentation. Further, based on historical analysis of temperature data and temperature conditions, a detection may be made that, given the current deviation, the electric motor may be overheating because of a faulty airflow fan. This root cause may be also associated with the indication and presented at the VR headset.

In the interest of clarity of explanation, embodiments of the present disclosure may be described using examples of a conveyor system of a storage, where the test equipment may be placed and moved between locations within the storage facility. However, the embodiments are not limited as such. Instead, the embodiments similarly apply to other material handling equipment and/or operational environments other than a storage facility. Generally, the test equipment may be used to check conditions associated with electrical and/or mechanical components of material handling equipment based on such components directly handling or causing a handling of the test equipment.

Figure 1:
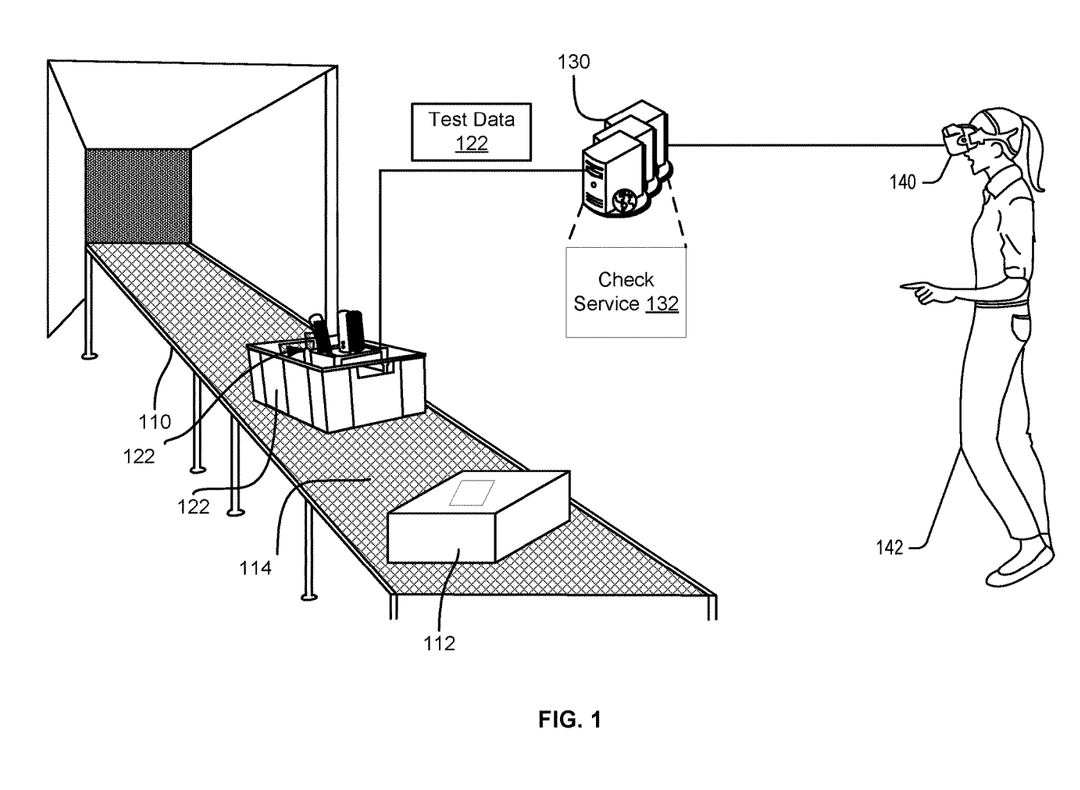
FIG. 1 illustrates an example system for checking different conditions based on sensed data, according to an embodiment of the present disclosure.

FIG. 1 illustrates an example system for checking different conditions based on sensed data. The system may include a conveyor system 110, test equipment 120, a computing resource 130, and user equipment 140. A user 142, such as an inspector, may operate the user equipment 140 to check conditions associated with the conveyor system 110. The conditions may be detected based on test data 122 generated by the test equipment 120. The test data 122 or an analysis of the test data 122 may be accessible to the user equipment 140 from the computing resource 130 via a check service 132. Faulty or unacceptable conditions may reflect a quality of the conveyor system 110. Generally, the test data 122 may be generated as part of commissioning and/or maintaining the conveyor system 110.

In an example, the conveyor system 110 may include various electrical components, such as electric motors, and mechanical components, such as rubber belts, rollers, sides, and other components. The conveyor system 110 may be located within a storage facility and may have a specific configuration. For instance, the configuration may include straight, serpentine, and/or spiral sections running at different heights across the storage facility. Generally, an item 112 may be placed on the conveyor system. Given the configuration, the conveyor system 110 may move the item 112 along a path 114 between locations within the storage facility. For instance, the path 114 may run from a source location that includes an inventory holder retaining the item to a destination location that includes an inventory station for receiving the item. Different electrical and mechanical components of the conveyor system 110 may facilitate the movement of the item 112 along the path 114.

In an example, the test equipment 120 may be configured to check conditions associated with the path 114. Such conditions may reflect whether the electrical and mechanical components of the conveyor system 110 along the path 114 have been properly installed and/or are properly operating. To do so, the test equipment 120 may be designed according to a particular size and to monitor particular conditions.

As far as the size, the test equipment 120 may be dimensioned (e.g., in volume and/or weight) to be similar to the dimensions of the item 112. Specifically, the conveyor system 110 may be installed to move items having dimensions that fall within a dimension range. Accordingly, the test equipment 120 may have dimensions that fall within the dimension range. In addition, some or all of the dimensions of the test equipment 120 may be adjustable to cover the lower and upper bounds of the dimension range. For instance, the test equipment 120 may include an adjustable frame that may be set to a particular height, width, and length. The test equipment 120 may also include a mount for retaining weight plates, such that the overall weight of the test equipment 120 may be adjusted to a particular weight given a particular number of retained weight plates. Generally, the dimensions of the test equipment 120 may enable placement of the test equipment 120 in a container 122 (e.g., a plastic container, a cardboard box, and the like), and the placement of the container 122 on a belt or rollers of the conveyor system 110.

As far as monitoring particular conditions, the test equipment 120 may include a plurality of sensors, a camera device, a power source, and a computing device (e.g., a processor, memory, and a transmitter) for sensing different types of data. Each type of data may indicate a condition (e.g., temperature data may indicate a temperature condition). A collection of different types of data may also indicate a condition (e.g., angle data and acceleration data may indicate a slippage condition). Generally, the sensors may capture measurements that the computing device may process to generate sensed data therefrom. The camera device may capture a video of a portion of the test equipment 120 and of the surrounding environment (e.g., a portion of the path 114). The sensed data and the captured image data (e.g., the video) may form the test data 122. The test data 122 may be further processed locally by the computing device and/or transmitted to the computing resource 130 for further processing thereat. The processing may enable a visualization of the test data at a user interface of the user equipment 140.

Different types of visualization may be possible. In an example, minimal processing of the test data 122 may be performed. In this example, the visualization may present the video, where the video may show the sensed data and the locations. In certain video segments, the video may show changes to the sensed data along with the respective location. Changes may indicate unacceptable conditions at these locations. In another example, more involved processing may be implemented. In this example, the processing may involve baseline test data, historical test data, and location data, in addition to the test data 122. The location data may be synchronized with the sensed data and may be derived by a location sensor or some other location means of the test equipment 122 or from the captured video. The processing may automatically identify the unacceptable conditions the respective locations, potential root causes, and may access troubleshooting documentations to resolve the root causes. The visualization may explicitly identify any of the unacceptable conditions (e.g., by showing an alert about an unacceptable conditions), the locations (e.g., by describing the location using location references of the storage facility), the potential root causes (e.g., an electric motor overheat), and troubleshooting information available from the documentations (e.g., replace an airflow fan). In yet another example, the processing may fall in between the minimal and the more involved implementations. For instance, the sensed data and the video may be sent as two different data streams to the computing resource 130. In turn, the computing resource 130 may generate an overlay of the sensed data over the video, where the overlay may show various meter readings or presentation formats to show the changes to the sensed data.

In an example, the computing resource 130 may be host the check service 132. The check service 132 may be configured as a computing service that may provide any of the above processing and that may facilitate the visualization to the user equipment 140. The computing resource 130 may be any suitable computing hardware, such as a server, or software hosted on hardware such as a virtual machine hosted in a datacenter. A data network may exist between the test equipment 120 and the computing resource 130 and between the computing resource 130 and the test equipment.

In an example, the test equipment 120 may stream the test data 122 live to the computing resource 130 over the data network, where the computing resource 130 may store and archive the test data 122. In another example, the test data 122 may be archived first at the test equipment and subsequently streamed to the computing resource 130. In a further example, the test equipment 120 may store the test data 122 on a storage device (e.g., a memory card). The storage device may be subsequently removed from the test equipment 120 and inserted into the computing resource 130, thereby moving the test data 122.

In an example, the user equipment 140 may be configured to interact with the check service 132. The interaction may provide the user equipment 140 with access to the test data 122 and/or any processing thereof. Thus, the interaction may enable any of the above visualizations at a user interface of the user equipment 140. The user equipment 140 may represent an end user computing device suitable for the interaction and for the visualization. For instance, the user equipment 140 may include a VR headset, a desktop, a laptop, a tablet, or other end user computing devices. Generally, the user equipment 140 may be remote from the test equipment 120 and the computing resource 130. As such, the user equipment 140 may be located at some location within the storage facility away from the conveyor system 100 and/or even outside of the storage facility (e.g., at a central maintenance/troubleshooting station or at a facility of the manufacturer's or installer of the conveyor system 110).

Figure 2:
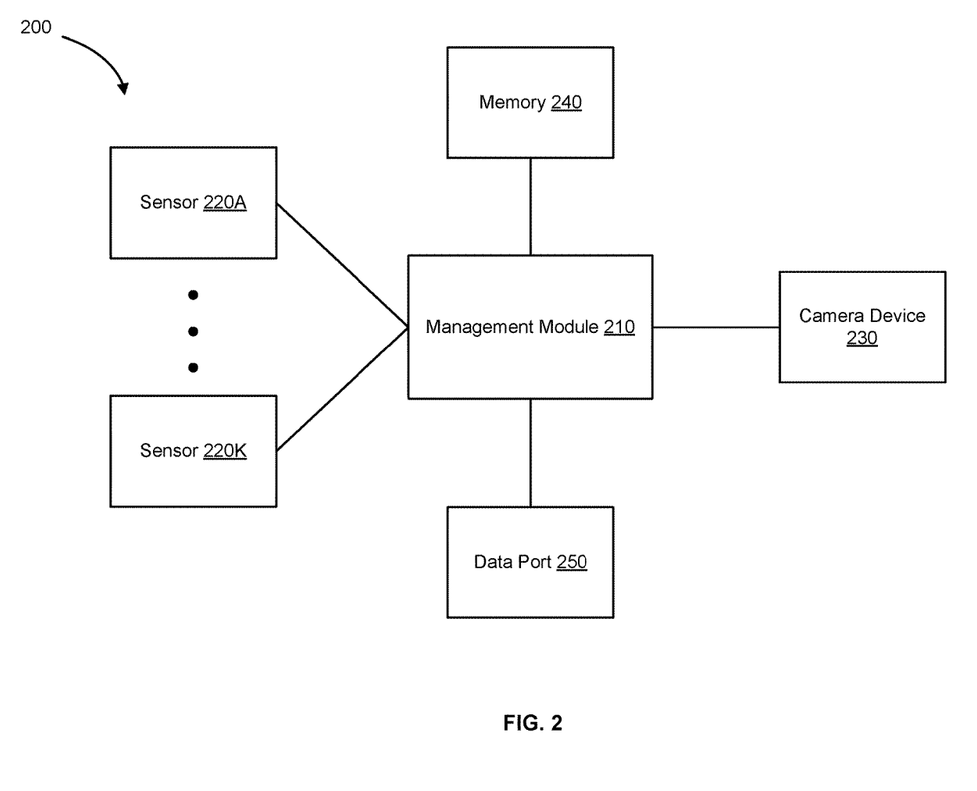
FIG. 2 illustrates example electrical components of test equipment, according to an embodiment of the present disclosure.
Figure 3:
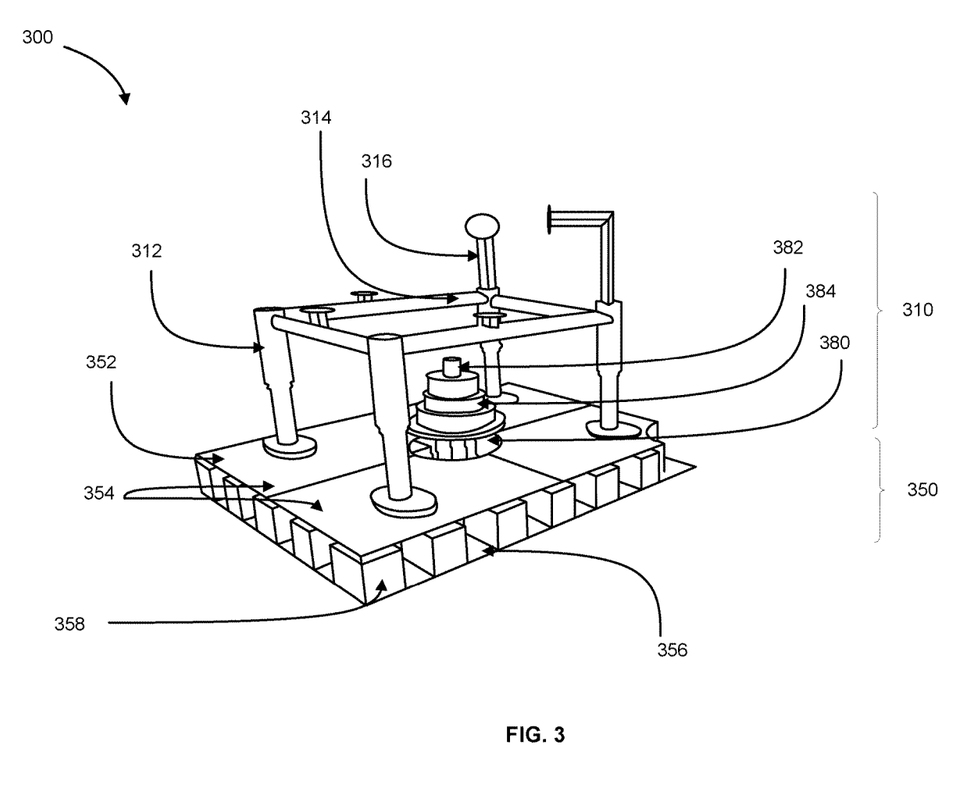
FIG. 3 illustrates example mechanical components of test equipment 300, according to an embodiment of the present disclosure.
Figure 4:
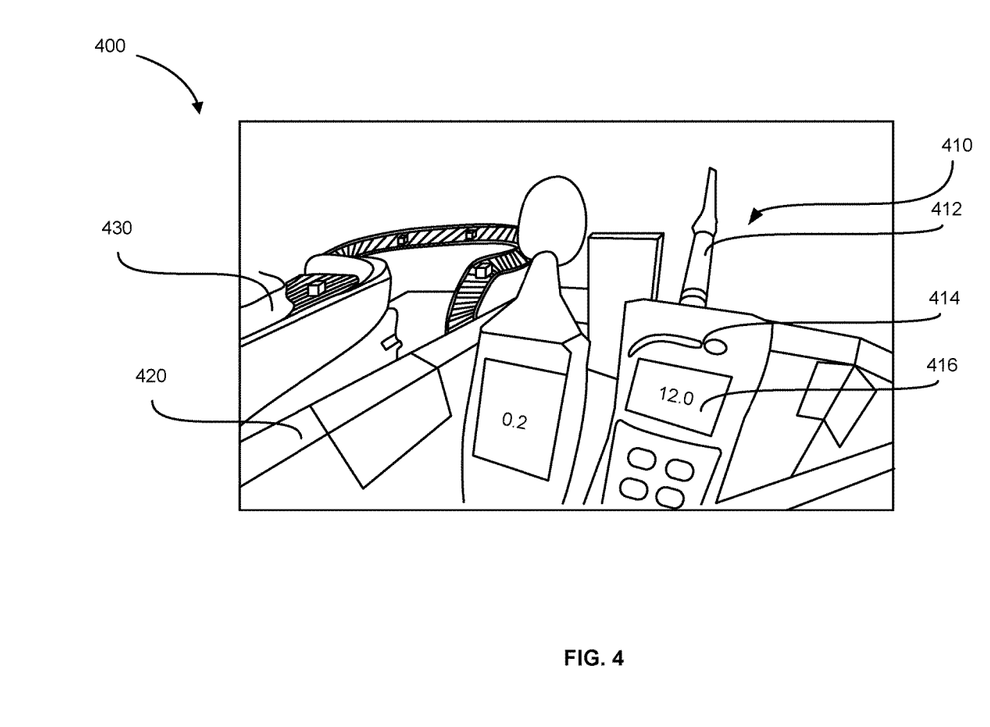
FIG. 4 illustrates an example visualization of test data, where the visualization may indicate a condition associated with a path along which test equipment may be moved, according to an embodiment of the present disclosure.
Figure 6:
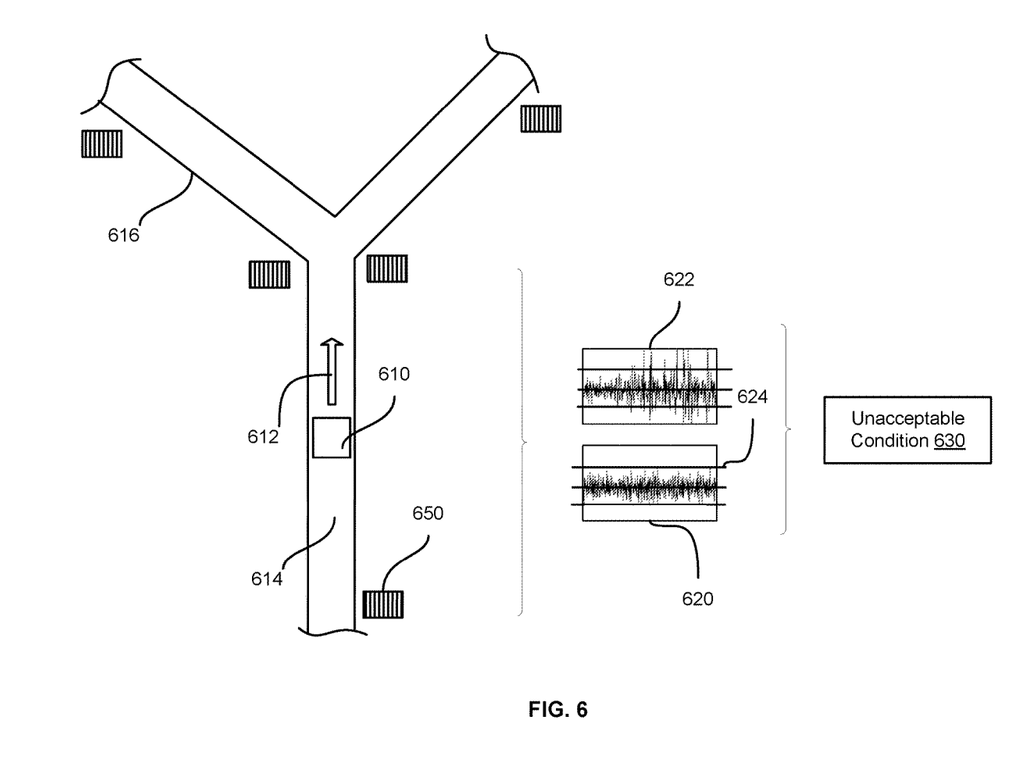
FIG. 6 illustrates an example set-up to detect conditions associated with a path, where the detection may rely on primarily sensed data and be supplemented with image data, according to an embodiment of the present disclosure.
Figure 7:
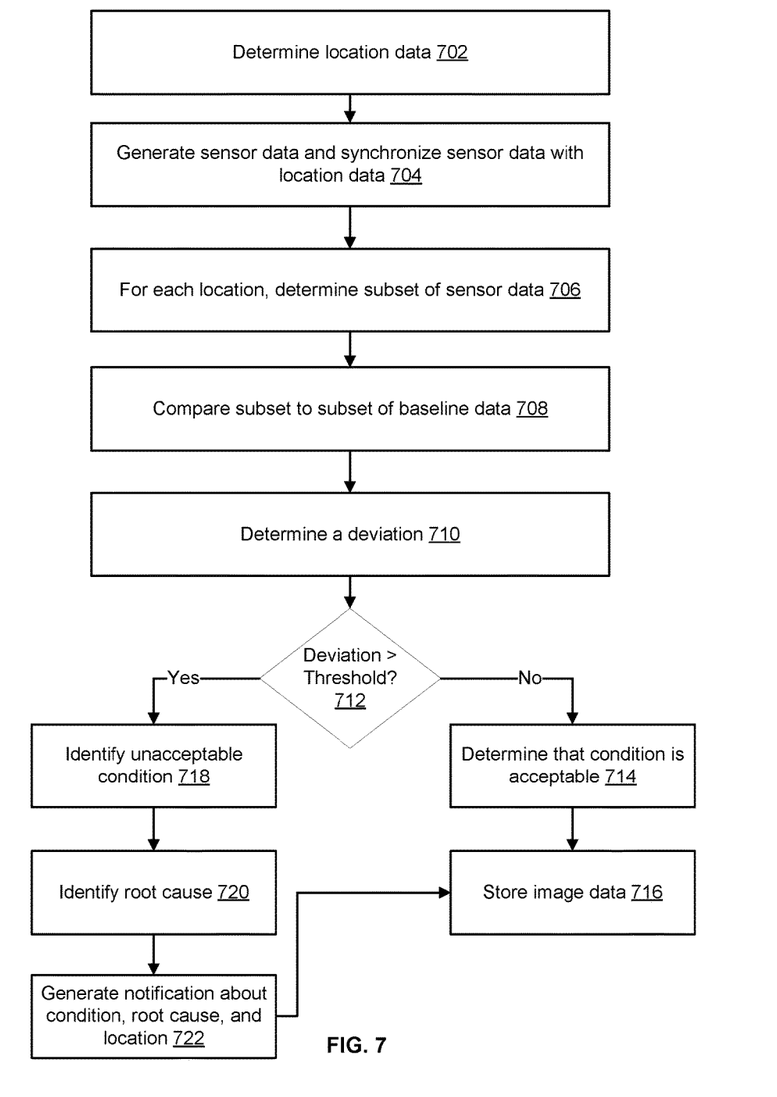
FIG. 7 illustrates an example flow for detecting conditions and associated locations along a path, according to an embodiment of the present disclosure.

As described herein above, the content of and analysis applied to the test data 122 may vary. In one example, the sensed data is shown as readings on user interfaces installed in the test equipment 120. The camera device of the test equipment may capture video of the readings and of the surrounding environment. The test data 122 may include the video and may be provided to the equipment device 140 via a transmission over a data network or streamed through the computing resource 130. FIGS. 2-4 further illustrate the example embodiment. In another example, the test data 122 may include the sensed data, location data, and image data (e.g., data forming one or more contiguous or non-contiguous video frames). In this example, the test data 122 may be analyzed locally at the test equipment 120 or remotely at the computing resource 130 to detect conditions, locations, and/or root causes of unacceptable conditions. In addition to, or in lieu of the test data 122, the output of the analysis may be provided to the user equipment 140 for visualization (or some other presentation modality). FIGS. 6-7 further illustrate the example embodiment.

FIG. 2 illustrates example electrical components of test equipment 200, such as the test equipment 140 of FIG. 1. The test equipment 200 may include a management module 210, sensors 220A-220K (collectively referred to as "sensors 220" or each as "sensor 220), a camera device 230, a memory 240, a data port 250, among other components (e.g., a power source). Some or all of the components may be integrated. For example, the management module 210 may be integrated with the camera device 230 or distributed across the camera device and the sensors 220. Generally, the management module 210 may control operations of the other components to receive measurements from the sensors 220, generate and display the sensed data at user interfaces, receive video from the camera device 230, store the video and/or sensed data in the memory 240, and transmit the video and/or the sensed data via the data port 250.

In an example, the sensors 220 may be of different types, where each sensor 220 may generate specific measurements. For instance, the sensors 220 may include a temperature sensor to measure temperature of the surrounding environment along a movement path of the test equipment 200, a pressure sensor to measure pressure applied to a surface of the test equipment 200, an impact sensor to measure impact from the surrounding environment against a surface of the test equipment 200, an acceleration sensor to measure an acceleration of the test equipment along the movement path, an angle sensor to measure an angle of the movement path, a height sensor, a height sensor (e.g., a laser distance sensor) to measure gaps and relative distances between a surface of the test equipment 200 and the surrounding environment, a vibration sensor to measure vibration along the movement path, a sound sensor to measure sound from the surrounding environment, a location sensor to measure a relative location of the test equipment 220, a distance sensor (e.g., a laser-based range sensor) to measure a distance between the test equipment 200 and a container on the path (e.g., a relative distance) and/or other types of sensors. The container may retain one or more items for movement along the path. In an example, each sensor 220 may be coupled with a processor, a memory, and a user interface (e.g., a screen), and a power source to form a meter. The meter may generate sensed data from the measurements of the sensor 220 and may display such data on the user interface as readings.

The camera device 230 may include a number of image sensors and processing circuitry to generate image data, such as video. For instance, the camera device 230 may be a three-hundred sixty degree camera capable of generating VR video. In an example, the management module 210 may display readings of the sensors 220 on user interfaces (e.g., screens). The user interfaces may be positioned around the camera device 230 (e.g., within the field of view of the camera device 230). Accordingly, the camera device 230 may generate a VR video of the different readings and the surrounding environment.

The memory 240 may store program instructions that are loadable and executable on the management module 221. The memory 240 may include a non-transitory computer-readable storage medium and may be volatile (such as random access memory (RAM)) and/or non-volatile (such as read-only memory (ROM), flash memory, or other memory). In addition, the memory 240 may store any test data, such as the measurements, sensed data, image data, location data and/or outputs of any analysis applied to the test data.

The data port 250 may represent a high speed interface that may be wired and/or wireless, serial and/or parallel and that may enable fast upload of the test data and download of command, computer-readable instructions, or data from remote computing resources and/or user equipment. In an example, the data port 250 may include universal serial bus (USB) ports, fiber optics ports, 802.11 IEEE standard interfaces, 802.16 IEEE standard interfaces, BLUETOOTH interfaces, near field communication interfaces, cellular interfaces, and/or other data ports along with appropriate circuitry (e.g., transmitters, receivers, encoders, decoders, etc.).

In an example, the management module 210 may include a processing logic such as a processor, microprocessor, multiple processing cores, FPGA, or otherwise. The management module 210 may be communicatively coupled to the other components of the test equipment 200. Computer-executable instructions, software or firmware implementations of the management module 210 may include computer-executable or machine-executable instructions written in any suitable programming language to perform the various operations described herein.

In an example, each sensor 220 may be a component of a meter having a screen for displaying measurements, while the camera device 230 may be a three-hundred sixty degree camera. The various meters may be positioned around the three-hundred sixty degree camera. As the test equipment 200 is moved by a conveyor system along a path for moving items, the three-hundred sixty degree camera may generate a VR video showing the screens and the path. The VR video may be sent via the data port 250 to a computing resource and/or user equipment.

Based on the displayed readings of the meters, the VR video may indicate different conditions and the respective locations along the path. For instance, the VR video may pinpoint noise location, vibration locations, speed change locations, hit/catch points, bounce locations, slippage locations, height clearances, and/or relative distances to containers on the path.

FIG. 3 illustrates example mechanical components of test equipment 300, such as the test equipment 140 of FIG. 1. Generally, the test equipment 300 may be dimensioned (in size and weight) to mimic dimensions of an item moved by a conveyor system. If the conveyor system supports a range of dimensions, the dimensions of the test equipment 300 may be adjustable within the range or different-dimensioned test equipment may be used.

In an example, the test equipment 300 may include a frame 310 sitting on a lower surface 350, each of which may have an adjustable size (e.g., in height, width, length) and an adjustable weight. The frame 310 may include a number of vertical mounts 312 and horizontal mounts 314, a number of pin holders 316. The vertical mounts 312 may be attached to the lower surface 350 (e.g., soldered, glued, screwed, bracketed, or other attachment interfaces). The height of the vertical mounts 310 may be adjusted upward or downward. In an example, the vertical mounts may be made of a rigid material, such as metal or hard plastic, and may have a hollow shape, such as a cylinder. The horizontal mounts 314 may be made of a similar rigid material, have a similar shape, and may be adjusted horizontally (e.g., in width or length depending on the relative location of a horizontal mount). Rather than being attached to the lower surface 350, the horizontal mounts 314 may be attached to the vertical mounts 312 and/or inter-attached to form a particular geometry of the frame 310 (e.g., a cuboid or some other three dimensional geometry). An end of a pin holder 316 may be attached to a horizontal mount 314 or a vertical mount 312. Another end of the pin holder 316 may be free and may be configured to attach a sensor (or, equivalently, a meter) or a camera.

To check for conditions, the test equipment 300 may be placed in a container or directly on the conveyor system. The lower surface 350 may act as a mechanical interface to the container and the conveyor system. In an example, the lower surface 350 may include a top layer 352, a bottom layer 356, and a material layer 358 in between. The vertical mounts 352 may attach to the top layer 352, which may be made of a rigid material. For instance, the top layer 352 may be a steel or hard plastic sheet. To enable adjustment, the rigid material may be cut into multiple pieces 354 that, when adjoined, form the top layer 352. Hence, and as illustrated in FIG. 3, if the width of the test equipment 300 should be increased, an adjoining sheet may be placed between the two sheets indicated with the arrow 354. The bottom layer 356 may be made of a similar material and may have a similar geometry. The material layer 358 may include material for damping any vibration from the interface (direct or indirect) of the test equipment 300 with the conveyor system. For instance, the material layer 358 may include a number of rubber cubes spaced in a checker arrangement.

To enable the weight adjustment of the test equipment 300, the top layer 352 may include an opening 380. A vertical mount 382 may be positioned in the opening 380 and attached to the bottom layer 356. Weight plates 384 may be mounted to and/or removed from the mount 382 as needed to achieve a desired weight.

In an example, the top layer 352 and bottom layer 356 may be made of sixteen gauge galvanized sheet metal and may have a substantially rectangular shape. The width and length of this shape may fall in the ranges of five to fifteen inches and eight to sixteen inches, respectively. The material layer 318 may be made of a number of one inch rubber cubes. The various mounts may be made of hard plastic. The vertical mounts 312 may have a substantially cylindrical shape with a radius and a height that may fall in the ranges of one fourth to one inch and four to ten inches, respectively. In comparison, the vertical mount 382 may have a similar shape but may be shorter (e.g., to keep the center of gravity low). For instance, the vertical mount 382 may have a height in the range of one to three and a half inches. The horizontal mounts 314 may have a similar shape with a length in the range of five to sixteen inches. The pin holders 314 may have variable heights and may include arms having variable lengths. The height may vary in the range of one fourth to four inches. The length of the arms may vary between half to two inches.

FIG. 4 illustrates an example visualization 400 of test data, where the visualization 400 may indicate a condition associated with a path along which test equipment may be moved. The test data may include a video showing readings displayed on screens of meters, where each meter may include one or more sensors and may display readings corresponding to the sensed data. In an example, the video may be a VR video, thereby enabling a three-hundred sixty degree stream of image data. The visualization 400 may correspond to a frame of the video, where the frame may be displayed at a user interface of user equipment, such as a screen of a VR headset.

The visualization 400 may show a portion of the test equipment 410 and a container 420 containing the test equipment 410. In addition, the visualization 400 may show a meter 414 attached to the test equipment 410 via a pin holder 412 and the readings 416 displayed by the meter 414. Further, the visualization 400 may show the surrounding environment 430.

Accordingly, a user may operate the user equipment to play the video. The visualization 400 of the video may indicate different conditions based on the shown readings 416 of the meters 416 and locations of these conditions based on the shown surrounding environment 430. A change to a reading 416 on a meter 414 may identify an unacceptable condition when the change is sudden and exceeds a certain threshold amount. The location in the surrounding environment 430 corresponding to the change may represent the location of the unacceptable condition. Other types of changes, or no change at, all may correspond to acceptable conditions. Therefore, the video may enable the user to quickly and efficiently ascertain the unacceptable conditions and the associated locations.

Figure 5:
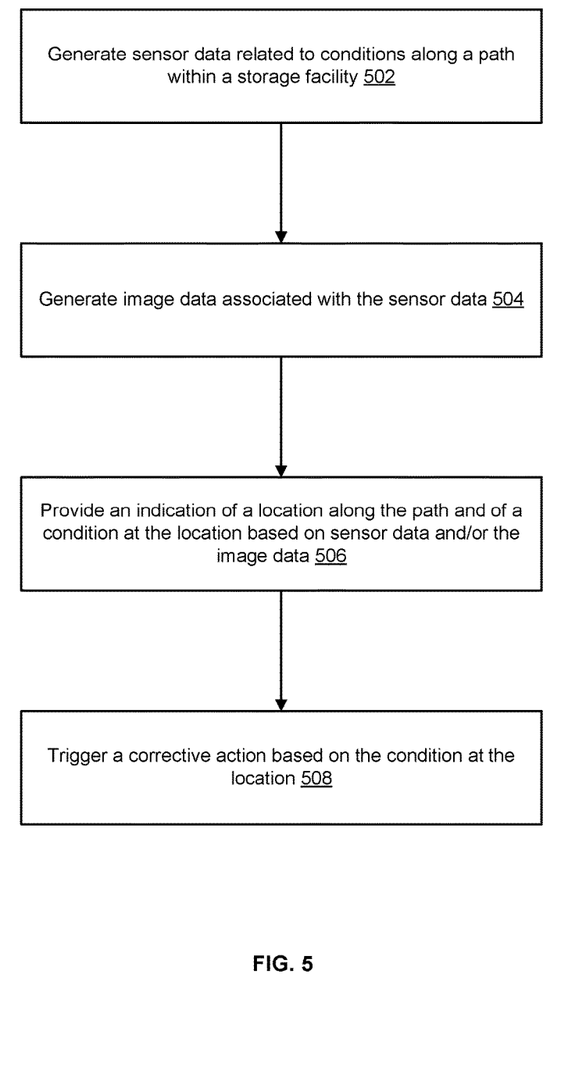
FIG. 5 illustrates an example flow for generating information about conditions and associated locations along a path and for triggering corrective actions based on the information, according to an embodiment of the present disclosure.

FIG. 5 illustrates an example flow for generating information about conditions and associated locations along a path and for triggering corrective actions based on the information. In the example flow, some of the operations may be embodied in, and fully or partially automated by, components of test equipment. While the operations are illustrated in a particular order, it should be understood that no particular order is necessary and that one or more operations may be omitted, skipped, and/or reordered.

The example flow may start at operation 502, where the test equipment may generate sensor data. In an example, the test equipment may be moved along a path by a conveyor system of a storage facility. The test equipment may be removably placed on the conveyor system for movement along the path. The same path may be used to move items. The test equipment may include a number of sensors. Accordingly, the test equipment may generate the sensor data from measurements captured by the sensors. The sensor data may relate to conditions along the path.

At operation 504, the test equipment may generate image data associated with the sensor data. The test equipment may include an image sensor or a camera device that generates the image data. The image data may represent a video or a set of images. In an example, the test equipment may display readings of the sensor data. The video (and, similarly, the images) may capture the readings and the surrounding environment. In another example, the test equipment may synchronize the image data and the test data. The synchronization may rely on the timing of when each data was generated. In this example, the test equipment may further synchronize the image data and/or test data with location data indicative of the location of the test equipment relative to the conveyor system.

At operation 506, the test equipment may provide an indication of a location along the path and of a condition at the location based on the sensor data and/or the image data. The indication may be provided to a computing resource and/or to user equipment.

In an example, the video (and, similarly, the images) may be transmitted via a data port of the test equipment. By showing the readings and the surrounding environment, indications of acceptable and unacceptable conditions and the respective locations may be visualized at a user interface. For instance, a change to a reading or multiple readings that may be sudden and/or increase a threshold value may indicate an unacceptable condition. A location shown in the video where the change occurred my correspond to the location of the unacceptable condition.

In another example, the test equipment or the computing resource may host a check service. The check service may analyze the video (and, similarly, the images) by using an image detection algorithm to track the readings and the changes thereto. The check service may compare the changes to threshold values and/or the readings to baseline readings. Unacceptable deviations (e.g., ones exceeding thresholds) may indicate unacceptable conditions. The check service may associate segments of the video showing the changes with the unacceptable deviations. An output of this analysis may be provided to the user equipment for visualization. The visualization may present the unacceptable deviations and the associated deviations, in addition to, or in lieu of the video.

In yet another example, the synchronized image data, sensor data, and location data may be analyzed by the check service. Rather than deriving the readings from a video, the check service may track changes to the sensor data, compare the changes to threshold values and/or the sensor data to baseline data, and, accordingly, detect unacceptable deviations. Based on the synchronization, the check service may associate relevant portions of the image data and location data with the unacceptable deviations. The visualization of the analysis output may present the unacceptable deviations, along with the relevant sensor data, image data (thereby showing the surrounding environment and identifying the relevant locations), and location data (thereby identifying the relevant locations).

At operation 508, the test equipment may trigger a corrective action based on any unacceptable condition and the associated location. In an example, by providing the video (and, similarly, images), the shown changes may trigger the user to troubleshoot the unacceptable condition(s) at the associated location(s). In another example, the check service may trigger similar corrective action by visualizing the unacceptable condition(s) and the associated location(s). Further, the check service may access a mapping of sensor data type, amount of deviation, and location to root causes and may access documentation storing information about troubleshooting the root causes. The check service may accordingly identify a root cause and a troubleshooting resolution for an unacceptable condition. As a corrective action to the unacceptable condition, the check service may also provide a visualization of the root cause and troubleshooting resolution and/or may generate a relevant troubleshooting ticket.

FIG. 6 illustrates an example set-up to detect conditions associated with a path 614, where the detection may rely on primarily sensed data 620 and be supplemented with image data. The path 614 may correspond to a movement 612 of test equipment 610 along a conveyor system 616. More particularly, a check service hosted on test equipment 610 or a computing resource may analyze the sensed data 320 generated from measurements of sensors of the test equipment 310. The analysis may involve comparing the sensed data 620 to baseline data 622 to identify changes. A change that exceeds a threshold value may indicate an unacceptable condition 630. Generally, the baseline data 622 may be defined from a proper commissioning of the conveyor system 616, a design of the conveyor system 616 or of the installation thereof, and/or historical test data collected through the commissioning and/or maintenance of the conveyor system 616 and other conveyor systems. The baseline data 622 may identify a range 624 of acceptable values (in magnitude or frequency) of the sensed data 622 per type or a combination of types of the sensed data 622. In other words, the baseline data 622 may represent a baseline signature of acceptable conditions along the path 614.

One example of a technical challenge of this analysis relates to a proper comparison of the sensed data 620 and the baseline data 622. Specifically, the baseline data 622 may correspond to locations or sections along the path 614. In other words, the baseline data 622 may be synchronized with location data along the path 614. Therefore, for a proper comparison, sensed data generated at a particular location or within a particular section should be compared to the relevant baseline data. An example solution to this technical challenge may involve synchronizing the sensed data 620 with the location data. Generally, the synchronization may involve detecting a location of the test equipment, correlating the sensed data with these locations, and storing the correlations.

Various techniques may be implemented to detect the location of the test equipment 610. In an example, triangulation, beaconing, or radar sensing (e.g., involving a Lidar) may be used. In another example, the location detection may be self-contained to the test equipment 610. In this example, the test equipment 610 need not rely on external or remote equipment to detect its location relative to the path 614. Instead, a three dimensional map of the conveyor system 616 and the different possible paths thereon may be loaded to a memory of the test equipment 610. The test equipment 616 may include a location meter having various sensors for sensing location-related data (e.g., a gyroscope, an accelerometer, a timer, etc.). The initial location where the test equipment 610 is placed on the conveyor system 100 may be entered via a user interface of the test equipment 610, transmitted remotely to the test equipment 610, and/or identified by a reader of the test equipment 610 (e.g., by an radio frequency identification (RFID) reader of the test equipment 610 reading an RFID tag at the initial location). Thereafter, the test equipment 616 may analyze the location-related data from the location meter (e.g., acceleration, orientation, direction, time, etc.) to track its location relative to the three dimensional map. That location may be used in the correlation with the sensed data 620.

In yet another example, fiducials 650 may also be used, as further illustrated in FIG. 6. A fiducial may represent a marking that encodes information about a location. For instance, the fiducial may include an RFID tag or a barcode. The fiducials 650 may be distributed at different locations along the path 614. The distribution may be continuous or may be segmented. For instance, one continuous fiducial strip or multiple individual fiducials may be attached to sides of the conveyor system 616. The test equipment 610 may include a fiducial reader, such as an RFID reader or a barcode reader, and may store a map of the fiducials. As the test equipment 610 moves along the path, the fiducial reader may read the fiducials 650. The encoded information may be derived from the fiducials and used to look up the location from the map. That location may be used as the relative location for the test equipment 610.

In an example of the segmented distribution, the fiducials 650 may be distributed along a repetitive pattern (e.g., every one foot) or at particular locations. These locations may correspond to a change in a component of the conveyor system 616 (e.g., a transition from a rubber belt to a metallic roller) or to a particular component thereof (e.g., an electric motor).

FIG. 7 illustrates an example flow for detecting conditions and associated locations along a path. The detection may rely primarily on sensor data generated from measurements of sensor test equipment. The detection may be further supplemented by image data generated from an image sensor (e.g., video from a camera device) of the test equipment. In the interest of clarity of explanation, the operations are described as being embodied in, and fully or partially automated by, components of the test equipment. However, the embodiments may not be limited as such. Instead, some of the operations may be distributed between the test equipment and a computing resource communicatively coupled with the test equipment or offloaded to the computing resource. More particularly, the test equipment and/or the computing resource may host a check service to analyze sensor data and, accordingly, detect the conditions. While the operations are illustrated in a particular order, it should be understood that no particular order is necessary and that one or more operations may be omitted, skipped, and/or reordered.

The example flow may start at operation 702, where the test equipment may determine its location data. The location data may correspond to locations of the test equipment during its movement along a path of a conveyor system. In an example, the location data may be generated by using any of the location detection techniques described in connection with FIG. 7 and may be stored in memory of the test equipment.

At operation 704, the test equipment may generate sensor data and may synchronize the sensor data with the location data. In an example, the test equipment may generate the sensor data from the measurements of the sensors and may correlate the sensor data with the location data while moving along the path.

At operation 706, the test equipment may determine a subset of the sensor data for a particular location. That location may correspond to a section along the path or to a particular point along the path. The subset of the sensor data may represent the relevant sensor data that corresponds to the location and may be determined from the synchronization. Operations 706-722 may be repeatedly performed to check and identify conditions along the entire path.

At operation 708, the test equipment may compare the subset of the sensor data to a subset of baseline data. The subset of baseline data may represent relevant baseline data that corresponds to the location and may be determined based on a synchronization of the baseline data with the location data. In an example, the baseline data may be generated based on a proper commissioning of the conveyor system, a design of the conveyor system or of the installation thereof, and/or historical test data collected through the commissioning and/or maintenance of the conveyor system and other conveyor systems. When historical test data is used, machine learning or some other data analysis technique may be implemented to generate the baseline data. For instance, the historical test data may track correct and incorrect installations and designs, sensed data, detected conditions, identified root causes, and/or troubleshooting resolutions. Machine learning may be applied to identify an acceptable range of sensed data (e.g., in magnitude or frequency) that may indicate acceptable conditions at high reliability or an acceptable likelihood.

At operation 710, the test equipment may determine a deviation between the two subsets of data. In an example, the deviation may be in magnitude or frequency and may be derived from the comparison.

At operation 712, the test equipment may determine whether the deviation may be acceptable or not. For example, the test equipment may compare the deviation to a threshold value. If lower than the threshold value, the deviation may be acceptable and operation 714 may be performed. Otherwise, operation 718 may be performed. The threshold value may be predefined based on the design, installation, and/or commissioning of the conveyor system and/or based on the analysis of the historical test data (e.g., by applying a machine learning algorithm).

At operation 714, the test equipment may determine that the condition may be acceptable. In an example, the test equipment may store an indication that the condition at the location was acceptable. At operation 716, the test equipment may store image data. The image data may capture the surrounding environment of the acceptable condition.

At operation 718, the test equipment may identify that the condition may be unacceptable. In an example, the test equipment may store an indication that the condition at the location was unacceptable.

At operation 720, the test equipment may identify a root cause of the unacceptable condition. For example, the test equipment may access from memory a mapping of sensor data type, amount of deviation, and location to root causes. Given the location and the type of the deviating sensor data, and the deviating amount, the test equipment may identify the root cause from the mapping.

At operation 722, the test equipment may generate a notification about the unacceptable condition, the root cause, and the location. The notification may be sent to a computing resource and/or to user equipment and may include the subset of the sensor data and the subset of the baseline data and may identify the unacceptable condition and the root cause. Further, the test equipment may access documentation storing information about troubleshooting the root causes and may identify therefrom a relevant troubleshooting resolution. The notification may describe the troubleshooting resolution. Operation 722 may also be followed by operation 716, where the test equipment may store image data about the surrounding environment of the unacceptable condition. The notification may include this image data too.

Figure 8:
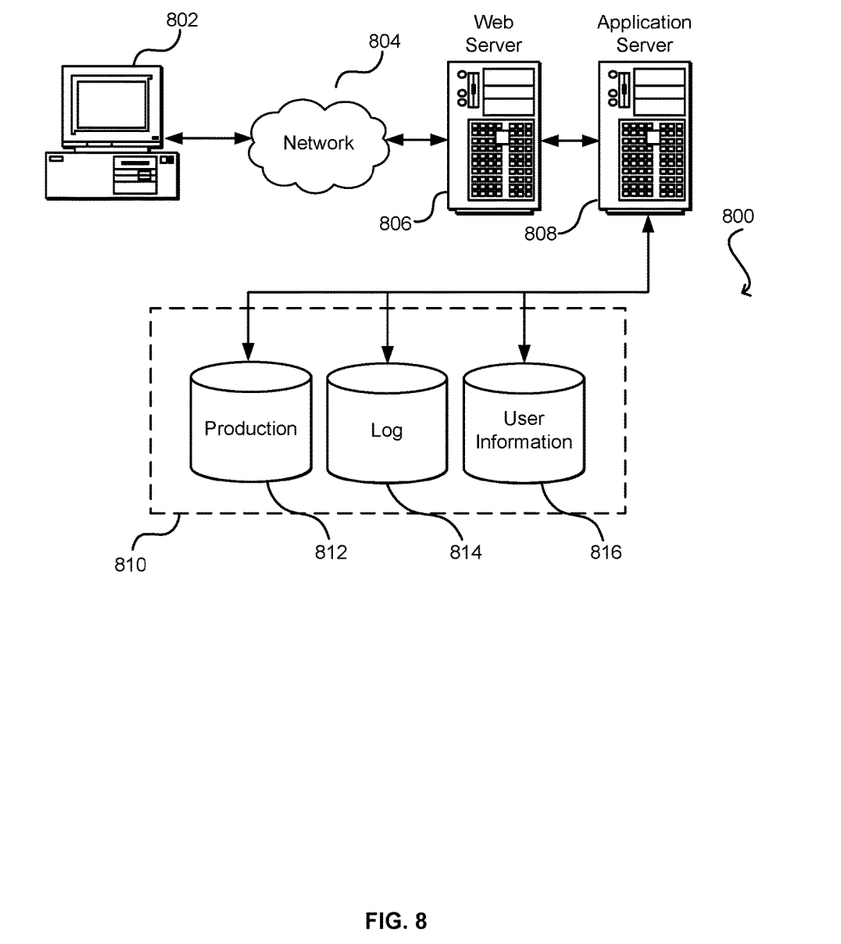
FIG. 8 illustrates aspects of an example computing environment for implementing aspects in accordance with various embodiments.

FIG. 8 illustrates aspects of an example computing environment 800 for implementing aspects in accordance with various embodiments. The computing environment 800 may host certain functionalities of a check service as described herein above. As will be appreciated, although a Web-based environment is used for purposes of explanation, different environments may be used, as appropriate, to implement various embodiments. The environment 800 includes an electronic client device 802, which can include any suitable device operable to send and receive requests, messages or information over a suitable network 804 and convey information back to a user of the device. Examples of such client devices include personal computers, cell phones, handheld messaging devices, laptop computers, set-top boxes, personal data assistants, electronic book readers, or other client devices. The network can include any suitable network, including an intranet, the Internet, a cellular network, a local area network or any suitable such network or combination thereof. Components used for such a system can depend at least in part upon the type of network and/or environment selected. Protocols and components for communicating via such a network are well known and will not be discussed herein in detail. Communication over the network can be enabled by wired or wireless connections and combinations thereof. In this example, the network includes the Internet, as the environment includes a Web server 806 for accessing requests and serving content in response thereto, although for other networks an alternative device serving a similar purpose could be used as would be apparent to one of ordinary skill in the art.

The illustrative environment includes at least one application server 808 and a data store 810. It should be understood that there can be several application servers, layers, or other elements, processes or components, which may be chained or otherwise configured, which can interact to perform tasks such as obtaining data from an appropriate data store. As used herein the term "data store" refers to any suitable device or combination of devices capable of storing, accessing and retrieving data, which may include any suitable combination and number of data servers, databases, data storage devices and data storage media, in any suitable standard, distributed or clustered environment. The application server can include any appropriate hardware and software for integrating with the data store as needed to execute aspects of one or more applications for the client device, handling a majority of the data access and business logic for an application. The application server provides access control services in cooperation with the data store and is able to generate content such as text, graphics, audio and/or video to be transferred to the user, which may be served to the user by the Web server in the form of HyperText Markup Language ("HTML"), Extensible Markup Language ("XML") or another appropriate structured language in this example. The handling of all requests and responses, as well as the delivery of content between the electronic client device 802 and the application server 808, can be handled by the Web server. It should be understood that the Web and application servers are not required and are merely example components, as structured code discussed herein can be executed on any appropriate device or host machine as discussed elsewhere herein.

The data store 810 can include several separate data tables, databases or other data storage mechanisms and media for storing data relating to a particular aspect. For example, the data store illustrated includes mechanisms for storing production data 812 and user information 816, which can be used to serve content for the production side. The data store also is shown to include a mechanism for storing log data 814, which can be used for reporting, analysis or other such purposes. It should be understood that there can be many other aspects that may need to be stored in the data store, such as for page image information and to access right information, which can be stored in any of the above listed mechanisms as appropriate or in additional mechanisms in the data store 810. The data store 810 is operable, through logic associated therewith, to receive instructions from the application server 808 and obtain, update or otherwise process data in response thereto. In some examples, a user might submit a search request for a certain type of item. In this case, the data store might access the user information to verify the identity of the user and can access the catalog detail information to obtain information about items of that type. The information then can be returned to the user, such as in a results listing on a Web page that the user is able to view via a browser on the electronic client device 802. Information for a particular item of interest can be viewed in a dedicated page or window of the browser.

Each server typically will include an operating system that provides executable program instructions for the general administration and operation of that server and typically will include a computer-readable storage medium (e.g., a hard disk, random access memory, read only memory, etc.) storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure herein.

The environment in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 8. Thus, the depiction of the environment 800 in FIG. 8 should be taken as being illustrative in nature and not limiting to the scope of the disclosure.

The various embodiments further can be implemented in a wide variety of operating environments, which in some cases can include one or more user computers, computing devices or processing devices which can be used to operate any of a number of suitable applications. User or client devices can include any suitable number of general purpose personal computers, such as desktop or laptop computers running a standard operating system, as well as cellular, wireless and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems and other devices capable of communicating via a network.

Most embodiments utilize at least one network that would be familiar to those skilled in the art for supporting communications using any of a variety of suitable commercially-available protocols, such as Transmission Control Protocol/Internet Protocol ("TCP/IP"), Open System Interconnection ("OSI"), File Transfer Protocol ("FTP"), Universal Plug and Play ("UpnP"), Network File System ("NFS"), Common Internet File System ("CIFS") and AppleTalk®. The network can be, for example, a local area network, a wide-area network, a virtual private network, the Internet, an intranet, an extranet, a public switched telephone network, an infrared network, a wireless network and any suitable combination thereof.

In embodiments utilizing a Web server, the Web server can run any of a variety of server or mid-tier applications, including Hypertext Transfer Protocol ("HTTP") servers, FTP servers, Common Gateway Interface ("CGI") servers, data servers, Java servers and business application servers. The server(s) also may be capable of executing programs or scripts in response to requests from user devices, such as by executing one or more Web applications that may be implemented as one or more scripts or programs written in any programming language, such as Java®, C, C# or C++, or any scripting language, such as Perl, Python or TCL, as well as combinations thereof. The server(s) may also include database servers, including without limitation, those commercially available from Oracle®, Microsoft®, Sybase® and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/ or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Storage media and computer readable media for containing code, or portions of code, can include any appropriate media known or used in the art, including storage media and communication media, such as but not limited to volatile and non-volatile, removable and non-removable media implemented in any suitable method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any suitable medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions, and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system comprising:
   material handling equipment configured to move an item between locations along a path of a storage facility;
   test equipment sized for movement by the material handling equipment along the path, the test equipment comprising a plurality of sensors and a camera device, the plurality of sensors configured to generate sensed data for different conditions along the path, the camera device configured to generate image data of the path, the test equipment better configured to transmit the image data based at least in part on the sensed data, the image data showing readings of data sensed by at least one sensor of the plurality of sensors; and
   user equipment remote from the test equipment and configured to receive and display the image data at a user interface, the displayed image data comprising an indication of at least one condition of the conditions, the at least one condition associated with a location along the path and affecting movement of the item at the location.

2. The system of claim 1, wherein the material handling equipment comprises a conveyor system to move the item between the locations, and wherein the conditions tested by the test equipment are associated with at least one of: noise, vibration, incline, speed, acceleration, hit points, catch points, bounce, slippage, height clearance, or relative distance to a container on the path.

3. The system of claim 1, wherein the camera device comprises a three-hundred sixty degree camera, wherein the plurality of sensors are positioned around the three-hundred sixty degree camera, wherein the image data represents an image stream of the path and of the sensed data from the plurality of sensors, and wherein the user equipment comprises a virtual reality headset configured to display the image stream.

4. The system of claim 1, wherein the test equipment is configured to stream the image data to the user equipment over one or more data networks, wherein the user equipment comprises a first user device located within the storage facility and a second user device located remote from the storage facility.

5. A computer-implemented method, comprising:
generating sensor data based at least in part on movement of test equipment by a material handling equipment along a path between locations, the test equipment removably placed on the material handling equipment for the movement along the path, the path associated with movement of an item by the material handling equipment, the sensor data associated with different conditions along the path, the test equipment comprising a plurality of sensors configured to generate the sensor data;
generating image data based at least in part on a camera device of the test equipment, the image data showing readings of data sensed by at least one sensor of the plurality of sensors; and
providing, based at least in part on the sensor data and the image data, an indication of a location along the path and of at least one condition from the different conditions, the at least one condition associated with the location along the path and affecting movement of the item at the location, the indication provided to a user equipment that is remote from the test equipment.

6. The computer-implemented method of claim 5, wherein the at least one condition is identified from the image data, wherein providing the indication comprises providing the image data to the user equipment, and wherein providing the indication triggers a corrective action to resolve the at least one condition.

7. The computer-implemented method of claim 6, wherein the test equipment comprises a plurality of user interfaces configured to display the sensor data, wherein the image data comprises an image stream of the plurality of user interfaces, and wherein the at least one condition is identified from the image stream based at least in part on a change to displayed sensor data on at least one of the plurality of user interfaces.

8. The computer-implemented method of claim 7, wherein the image stream identifies the path, and wherein the location associated with the at least one condition is identified based at least in part on the image stream.

9. The computer-implemented method of claim 5, further comprising:
generating location data of the test equipment along the path; and
synchronizing the sensor data and the location data of the test equipment, wherein the location associated with the at least one condition is identified based at least in part on the synchronizing.

10. The computer-implemented method of claim 9, further comprising:
identifying the location along the path based at least in part on the location data;
identifying a subset of the sensor data that corresponds to the location based at least in part on the synchronizing;
detecting a deviation between the subset of the sensor data and a subset of baseline data that corresponds to the location; and
detecting the at least one condition based at least in part on the deviation.

11. The computer-implemented method of claim 10, wherein the at least one condition is detected based at least in part on a comparison of the deviation to a deviation threshold, wherein the deviation threshold is defined based at least in part on historical sensor data and historical conditions or on a design parameter of the material handling equipment.

12. The computer-implemented method of claim 10, further comprising:
displaying the indication at a user interface of the user equipment, wherein the displayed indication identifies the at least one condition, comprises at least one of the subset of the sensor data or the deviation, and comprises an image of the location.

13. The computer-implemented method of claim 10, further comprising:
detecting a root cause of the at least one condition based at least in part on the deviation and on historical deviations between historical sensor data and historical baseline data; and
providing information about the root cause for presentation at a user interface of the user equipment.

14. The computer-implemented method of claim 9, further comprising:
detecting, by the test equipment, fiducials that are along the path and that are attached to the material handling equipment, wherein the location data is generated by the test equipment based at least in part on fiducials.

15. A test apparatus comprising:
a frame sized for movement of the test apparatus by a material handling equipment along a path between locations of a storage facility, the path associated with movement of an item by the material handling equipment;
a plurality of sensors connected with the frame, the plurality of sensors configured to generate sensor data based at least in part on the movement of the test equipment, the sensor data associated with different conditions along the path;
a camera device configured to generate an image stream of the sensor data; and
a data port configured to provide, based at least in part on the sensor data and the image stream, an indication of a location along the path and of at least one condition of the conditions, the at least one condition associated with the location along the path and affecting movement of the item at the location.

16. The test apparatus of claim 15, wherein the indication is provided to user equipment associated with the material handling equipment, and wherein providing the indication causes the user equipment to display the location and the at least one condition at a user interface.

17. The test apparatus of claim 15, wherein the plurality of sensors are positioned around the camera device, and wherein the data port is further configured to provide the image stream.

18. The test apparatus of claim 15, wherein the frame comprises a plurality of mounts positioned over a bottom surface of the frame and a plurality of pins configured to interface with the plurality of sensors.

19. The test apparatus of claim 18, wherein the bottom surface is defined by a plate mounted on a vibration damping material.

20. The test apparatus of claim 18, wherein the bottom surface comprises an opening, and wherein a mount is positioned in the opening and is configured to retain an adjustable number of weight plates.

* * * * *